United States Patent [19]

Kim

[11] 4,010,742
[45] Mar. 8, 1977

[54] ELECTRON THERAPY DEVICE

[76] Inventor: In Su Kim, 54-1, 2-ka, Myeong-dong, Junk, Seoul, South Korea

[22] Filed: July 15, 1975

[21] Appl. No.: 596,164

[30] Foreign Application Priority Data

July 29, 1974   South Korea ............... 743200

[52] U.S. Cl. ......................................... 128/24.4
[51] Int. Cl.² ....................................... A61H 29/00
[58] Field of Search ............ 128/24.2, 24.4, 24.5, 128/32, 41

[56] References Cited

UNITED STATES PATENTS

| | | | |
|---|---|---|---|
| 637,321 | 11/1899 | Casper | 128/24.4 |
| 852,163 | 4/1907 | Buchanan | 128/24.4 |
| 1,000,294 | 8/1911 | Rosenberg | 128/24.5 X |
| 1,230,283 | 6/1917 | Davidson et al. | 128/24.5 |
| 2,523,547 | 9/1950 | Zerkle | 128/24.5 |
| 2,553,873 | 5/1951 | Schwebel | 128/24.4 |

Primary Examiner—Lawrence W. Trapp
Attorney, Agent, or Firm—Cameron, Kerkam, Sutton, Stowell & Stowell

[57] ABSTRACT

An electron therapy device for the treatment of various ailments of the human body has a vibrator including a source of heat and an electrical circuit which supplies electrons to the skin of the human body by means of rollers which contact the skin so as to overcome a deficiency of electrons in the body and help maintain a state of equilibrium of electron current within the body.

6 Claims, 3 Drawing Figures

ELECTRON THERAPY DEVICE

It is generally recognized that there are micro negative and positive electric currents running throughout the human body, and that these electric currents are a vital factor in controlling the function of cells in the human body. However, when a human body shows symptoms in metabolism caused by unnecessary additives, or by outside stimulus, or by infection by microbes, it is susceptible to disease. This creates a strain or paralysis of body metabolism which in turn changes the state of equilibrium and the distribution of electronic current in the human body. For example, the portion of the body which is inflamed and/or develops fever will contain an excessive electron current concentrated on that part of the body. This phenomenon is known as a condition of strain caused by exacerbation of proper metabolism function.

Giving impetus to cells in living organisms may cause functioning excitement. As impetus increases, portions or given parts of a living organism may be affected by such excitement. When impetus increases, and excitement function correspondingly increases, there will be changes in value of the electric current running within the living organism, and electric current will therefore be concentrated on the portion or part of the organism which has become excited. A living body takes in necessary substances from the exterior which are dissolved, absorbed and assimilated, and thereby takes in necessary calories. Substances taken into living organisms from the outside must be oxidized in order to obtain necessary calories. The force of electrons is deemed a vital factor in this process.

Of the two characteristics of the electron, a positron is used in the course of resolving substances, while a negatron is used in the course of oxidation of substances. To produce energy in living organisms a negatron is necessry, although both positrons and negatrons have been found in the cells of living organisms and help control the functions of the cells. However, a large quantity of negatrons is requied to oxidize and absorb substances taken into the organism from the outside.

It is commonly recognized that when a proper balance of negatrons is maintained within a living organism, it is considered healthy. But if there exists a shortage of negatrons, cell function is paralyzed because of a shortage of calories being taken in and oxidized. Positrons are necessary to eliminate waste from the body. However, if in the course of oxidation there are more positrons than negatrons, necessary calories would be reduced, the eliminating function would be affected, and hence functioning of the living organism would become gradually paralyzed.

The object of the present invention is to provide the body with pure electrons while completely eliminating unnecessary positrons, and to supply necessary calories for the human body onto the skin. Compared to conventional methods of dissolving the substances taken into the human body, use of the present invention expedites cell functioning and enables the body to withstand the influx of harmful germs into the body from the outside, and so enables the body to protect itself. Cells in the human body can be excited by giving impetus to them, and can obtain energy by this excitement functioning, thus assimilating and absorbing substances taken into the human body from outside and then eliminating waste matter from the body. However, this function is only able to be maintained under limited conditions. For example, excessive excitement state may be caused by the application of immoderate impetus, or by unnecessary substances taken into the human body. Internal organs would then be unable to function due to exhaustion and a weakening state, and the function of the living organism would gradually deteriorate and become paralyzed because of an insufficient supply of necessary energy.

By using conventional methods or means, necessary impetus to help paralyzed or deteriorated cells is given by applying medicinal substances or physical means. However, while the use of such methods provides some help to the excitement function, it is unable to supply sufficient necessary calories. When germs or unnecessary substances are taken in by the body, the body experiences a rise in temperature due to the excitement of the central nerve. A symptom of excitement in the central nerve could be restrained or tranquilized to reduce unnecessary consumption of calories by use of conventional means, but the latter is unable to supply vitality to the cell function physically.

Based on the foregoing considerations affecting the well being of the human body, the present invention relates to an electronic therapy device designed for the remedy of various diseases by physically applying proper electrons onto the human body from the exterior, thereby replenishing any deficiency of electrons in the body and thus maintaining a state of equilibrium of electron current within the body.

Referring now to the drawings.

Figure 1:
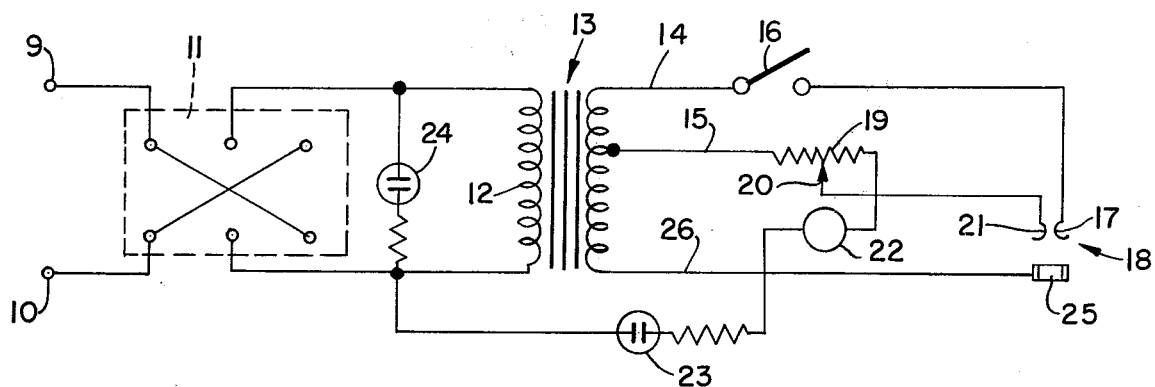
FIG. 1 is a circuit drawing of a power pack for providing a source of 6-volt and 9-volt, 60 cycle current to be provided to the vibrator and electron applicator of FIG. 2.

Referring now to FIG. 1, the power pack illustrated therein comprises a pair of terminals 9 and 10 adapted to be connected to any convenient source of 110 volts, 60 cycle alternating current. Terminals 9 and 10 are connected to the cross-connected stationary contacts of a double-pole double-throw switch 11, the center contacts of which are connected to the primary coil 12 of a power transformer 13. The secondary of transformer 13 is provided with a 9-volt take-off line 14 and a 6-volt take-off line 15, the 9-volt line 14 leading via a vibrator switch 16 to the 9-volt contact 17 of a jack socket 18. The 6-volt take-off line 15 is connected to one end of the resistance element of a rheostat 19 the movable contact 20 of which is connected to the 6-volt 21 of jack socket 18. the other end of the resistance element of rheostat 19 is connected via a heat indicator meter 22, an electron signal neon lamp 23 and associated resistance, and a power signal neon lamp 24 and associated resistance to one of the leads from the switch 11 to the primary coil 12 of transformer 13. The sleeve 25 of jack socket 18 is connected via the return lead 26 to the secondary of transformer 13. The device thus supplies 6-volt and 9-volt power to the jack socket 18.

Figure 2:
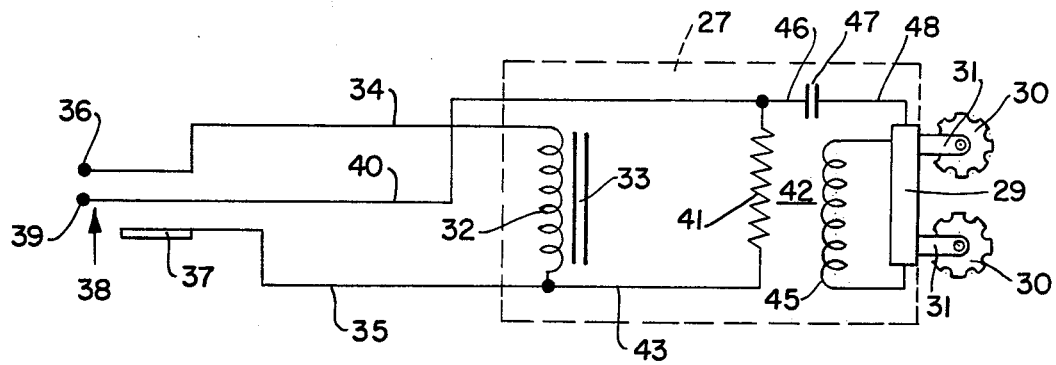
FIG. 2 is a circuit diagram of a vibrator and applicator adapted to be connected to the output of FIG. 1 and to be manually applied to the skin of the human body to supply vibration, electrons and heat thereto.
Figure 3:
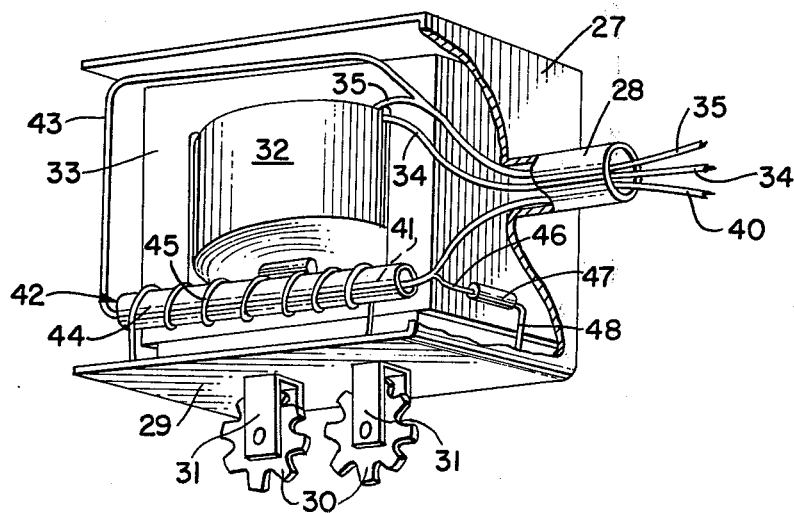
FIG. 3 is a perspective view, partially broken away, of the vibrator and applicator embodying the circuit of FIG. 2.

Referring now to FIGS. 2 and 3, the vibrator-applicator of the present invention comprises a vibrator casing 27 having a handle 28, a vibratory panel 29 and a pair of rollers 30 connected to the panel 29 by means of brackets 31. The panel 29, rollers 30 and brackets 31 are made of stainless steel or other suitable electrically conductive material. Housed within casing 27 are the coil 32 and core 33 of a vibrator, the core 33 being mounted on the vibratory panel 29 so as to transmit vibration to the latter. Coil 32 is connected to leads 34 and 35 which are in turn connected to the 9-volt contact 36 and sleeve 37, respectively, of a jack plug 38 wich is adapted to be inserted in the jack socket 18 of FIG. 1 in order to provide power to the elements of FIGS. 2 and 3.

6-volt contact 39 of jack plug 38 is connected via line 40 to one end of the resistor 41 of a heater 42, the other end of the resistor being connected by a line 43 to lead 35 from contact 37 of jack plug 38. Contact 39 and line 40 provide 6-volt power to the heater. Resistor 41 is surrounded by a glass pipe 44 which is in turn surrounded by a coil 45 mounted on vibratory panel 29 so as to conduct heat at a temperature of 40° C to the panel. The end of resistor 41 opposite that to which lead 43 is connected is connected via a lead 46 to one side of a capacitor 47 the other side of which is connected by a lead 48 to the vibratory panel 29.

In using the device of the present invention, the terminals 9 and 10 of the power pack are connected to a source of 110 volts, 60 cycle alternating current which, when switch 11 is closed, provides current to the primary coil 12 of transformer 13, the secondary of which transformer in turn provides 6-volt and 9-volt power to lines 15 and 14, respectively. With this arrangement, 6-volt power is supplied to contact 21 of jack socket 18 and, when vibrator switch 16 is closed, 9-volt power is supplied to contact 17 of the jack socket. When jack plug 38 is plugged into jack socket 18, 9-volt alternating current power is supplied to vibrator coil 32 which, through core 33, sets up vibrations in vibratory panel 29. At the same time, 6-volt power is supplied from jack plug contact 39 to resistor 41 of heater 42, the heat generated by the heater being conducted to panel 29 through coil 45. At the same time, 6-volt current is supplied to capacitor 47 which breaks the current but permits electrons to flow though the line 48 to the panel 29 and rollers 30. When, by use of the handle 28, the rollers are applied to the skin of a human being, electrons are supplied to the skin. At the same time heat of about 40° C is also supplied to the rollers from coil 45. When electrons are being applied to the skin, electron signal lamp 23 is extinguished so that the user of the device can tell whether or not the device is working. When the apparatus is ready for use both electron signal lamp 23 and power signal lamp 24 are illuminated, but when the rollers 30 are contacted with either the human skin or ground, electron signal lamp 23 is extinguished indicating that electrons are penetrating into either the skin or ground.

There is thus provided by the present invention a device for supplying electrons, vibration and heat to the human skin, thereby giving tone to skin which has been strained and promoting exacerbation functioning of the weakened body. The strained or paralyzed skin or muscle of the human body is thereby rehabilitated, while at the same time a state of equilibrium of electron current in the body is maintained. Favorable results have been obtained by the use of the apparatus of the present invention in the treatment of such ailments of the human body as hypertension, neuralgia and sciatica.

What is claimed is;

1. An electron therapy device for the treatment of ailments of the human body comprising a vibrator including a casing having a vibratory panel of conductive material, electrically energized means housed in said casing for imparting vibration to said panel, applicator means of conductive material mounted on said panel for contact with the human body, and means for supplying negative electrons only to said panel and applicator means whereby, when said applicator means are brought into contact with the human body, negative electrons are introduced into the body.

2. An electron therapy device as claimed in claim 1, including means for supplying heat to said panel and applicator means.

3. An electron therapy device as claimed in claim 1 wherein said applicator means comprises at least one roller rotatably mounted on said panel.

4. An electron therapy device as claimed in claim 2 wherein said heating means includes an electrically energized resistor, and said means for supplying negative electrons to said panel and applicator means includes a single conductor connecting one end of said heating resistor to said panel, and a capacitor in series with said conductor between said one end of said heating resistor and said panel.

5. An electron therapy device for the treatment of ailments of the human body comprising an electrical circuit providing a source of low voltage alternating current, applicator means of conductive material for contact with the human body, and means for connecting said applicator means to the negative side only of said circuit whereby, when said applicator means are brought into contact with the human body, negative electrons are introduced into the body.

6. An electron therapy device as claimed in claim 5 including a single conductor conecting the negative side of said electrical circuit to said applicator means, and a capacitor in series with said conductor between said negative side of said electrical circuit and said applicator means.

* * * * *